US006960226B2

(12) United States Patent
Ward

(10) Patent No.: US 6,960,226 B2
(45) Date of Patent: Nov. 1, 2005

(54) APPARATUS FOR RELIEVING THE SYMPTOMS OF DEEP VEIN THROMBOSIS

(75) Inventor: Derek Alfred Ward, Dover (GB)

(73) Assignee: Environmental Seals Ltd., (GB)

( * ) Notice: Subject to any disclaimer, the term of this patent is extended or adjusted under 35 U.S.C. 154(b) by 84 days.

(21) Appl. No.: 10/475,748

(22) PCT Filed: Jul. 2, 2002

(86) PCT No.: PCT/GB02/03038

§ 371 (c)(1),
(2), (4) Date: Oct. 24, 2003

(87) PCT Pub. No.: WO03/003955

PCT Pub. Date: Jan. 16, 2003

(65) Prior Publication Data

US 2004/0133257 A1    Jul. 8, 2004

(30) Foreign Application Priority Data

Jul. 6, 2001  (GB) .................................... 0116484

(51) Int. Cl.⁷ .............................................. A61F 7/00
(52) U.S. Cl. .................... 607/114; 607/104; 607/108
(58) Field of Search ........................................ 607/114

(56) References Cited

U.S. PATENT DOCUMENTS

| | | | | |
|---|---|---|---|---|
| 3,987,506 A | * | 10/1976 | Markwitz | .................... 601/149 |
| 4,003,374 A | * | 1/1977 | Mizrachy | ...................... 601/89 |
| 4,619,055 A | * | 10/1986 | Davidson | ........................ 36/28 |
| 4,993,409 A | * | 2/1991 | Grim | ............................ 602/19 |
| 5,275,315 A | * | 1/1994 | Carmack et al. | ............ 224/576 |
| 5,415,624 A | | 5/1995 | Williams | ...................... 602/21 |
| 5,846,063 A | * | 12/1998 | Lakic | .......................... 417/440 |
| 6,592,534 B1 | * | 7/2003 | Rutt et al. | .................. 601/151 |
| 6,615,080 B1 | * | 9/2003 | Unsworth et al. | ............. 607/2 |

FOREIGN PATENT DOCUMENTS

| | | |
|---|---|---|
| GB | 1 310 492 | 3/1973 |
| GB | 2 245 497 | 1/1992 |
| GB | 2 263 405 | 7/1993 |
| GB | 2 327 888 | 2/1999 |
| WO | WO 01/08613 | 2/2001 |

* cited by examiner

Primary Examiner—Henry M Johnson, III
(74) Attorney, Agent, or Firm—Blank Rome LLP

(57) ABSTRACT

Apparatus for relieving the symptoms of deep vein thrombosis comprises a fabric envelope having on one surface a plurality of projections and on an opposed surface, one or more strips of a hook and loop-type fastener sold under the trademark Velcro® or similar material for releasably attaching the envelope to a carpeted floor surface. A container fits within the fabric envelope and comprises two side-by-side compartments which communicate with one another through one or more openings. A mouthpiece is provided in the container to enable the compartment to be inflated. The container includes a pocket above one of the two compartments of the container to receive a heating element.

9 Claims, 3 Drawing Sheets

APPARATUS FOR RELIEVING THE SYMPTOMS OF DEEP VEIN THROMBOSIS

This invention relates to apparatus for relieving the symptoms of deep vein thrombosis.

It is widely appreciated that being seated in relatively confined spaces for long periods of time can lead to deep vein thrombosis, namely coagulation of blood in a blood vessel or organ. Airline passengers on long haul journeys have suffered from this condition, popularly referred to as "Economy Class Syndrome". The condition is believed to arise through lack of exercise of the feet and legs and pressure applied consistently to the soles of a person's feet or the back of a person's knees by the edge of the seat in which the person is positioned.

Devices seeking to prevent or reduce deep vein thrombosis have been proposed previously. These proposals include a compression system for increasing blood flow as disclosed in GB-A-2327888, an inflatable compression garment as disclosed in GB-A-2271060, and an ambulatory pneumatic compression device as disclosed in GB-A-2263405. In the first and second of these documents, blood circulation in a limb is stimulated by a periodically inflatable sheet which is wrapped around a patient's foot. This is cumbersome to apply and requires an external pressure source. It is, therefore, inappropriate for aircraft travel. GB-A-2263405 concerns an orthopaedic shoe connected to recipient cells wrapped around the calf and ankle of a user and operable to exert a pumping effect to the cells as the user walks. Again, such a device is inappropriate for air travel.

The present invention sets out to provide apparatus capable of preventing, or at least reducing the likelihood of, deep vein thrombosis in airline passengers and others, which is easy to use, does not require an external pressure source for operation and does not present a danger to the safety of passengers when used in, for example, the confines of an aircraft cabin.

According to the present invention in one aspect, there is provided apparatus for relieving the symptoms of deep vein thrombosis which comprises a container including first and second compartments each at least partially filled with a flowable material and each produced at least partially from a resilient material, an envelope housing the compartments, and a pocket for receiving a heating element which overlies only one compartment of the container, an external surface of the envelope being formed with ribs, serrations or like projections.

The interiors of the compartments may be placed in communication with one another through one or more communicating passageways.

The envelope may be produced from a fabric, e.g. a woven fabric and the ribs may be formed from a plastics material, from synthetic rubber, or a rubber substance.

The compartments may be separated by a seam extending between sides of the container. Preferably the compartments are aligned one alongside the other. If the compartments are separated along a seam, the seam may be partially discontinuous to define the communicating passageways.

Each container may be produced from a rubber or resilient plastics material and may be permanently sealed or fitted with a removable plug, stopper or the like. A mouthpiece may be provided to enable the interior of the container to be filled with air by the user blowing air by mouth into the container via the mouthpiece.

Alternative flowable materials include water or a solid granular material may be employed. One compartment may, for example, contain water and the other air. Preferably, each compartment contains air.

A heating element may be permanently or releasably located within the pocket. Operation of the heating element produces a difference in temperature to exist between the contents of the two compartments. Preferably, the heating element comprises a portable heat pack which comprises a sealed flexible plastics bag containing a chemically reactive substance (typically sodium acetate) and a metallic disc which when subjected to finger pressure or flexing produces a chemical reaction within the reactive substance to generate heat. Typically, the heat generated persists for periods in excess of thirty minutes. After this, the bag and the contents can be reactivated simply by placing the bag in boiling water. The bag can then be reused.

Means may be provided to attach the underside of the envelope to a floor surface. This may comprise one or more suitably positioned pieces of a hook and loop-type fastener sold under the trademark Velcro®.

The container may be wholly produced from a resilient material; alternatively, the upper surfaces of each container may be produced from resilient material. The shape and dimensions of the container and that of the envelope are preferably such as to enable a seated user to place his or her feet on the upper surfaces of the containers, downward movement of the user's toes causing the respective heel to lift and vice-versa. This action is assisted if the interiors of the containers are in communication with one another.

The ridges or other projections formed on an outer surface of the envelope enable a user to rub his/her feet over the ridges to encourage blood circulation, and the heating element (if used) produces a temperature differential between the feet of the user which again encourages circulation.

In a preferred embodiment of the invention, the apparatus comprises a container of a rubber-like material located within an open-ended material envelope. The container includes two compartments placed in communication with one another through a partially discontinuous seam. In this embodiment both of the compartments are filled with air. One compartment includes a mouthpiece to enable air to be blown by mouth into that compartment and into the other compartment via the communicating passageways or vents produced by the partially discontinuous seam. The envelope carries on its lower surface strips of a hook and loop-type fastener sold under the trademark Velcro® to enable it to be secured to a carpeted floor surface immediately in front of, for example, an airline seat and positioned to enable the user of the seat readily to place his or her feet on the enveloped compartments of the container. The container has an exterior pocket positioned over one of the compartments for receiving a heating element which operates to raise the temperature of the contents of that compartment. The heating element comprises a portable heat pack which comprises a sealed flexible plastic bag containing a chemically reactive substance (typically sodium acetate) and a metallic disc which when subjected to finger pressure or flexing produces a chemical reaction within the reactive substance to generate heat.

In use of the preferred embodiment, the user of the apparatus places his or her feet on the envelope above the compartments of the container than then flexes his or her feet thereby inducing a rocking movement which encourages the flow of blood through the person's body. The temperature difference caused by the presence of the heating element also encourages flow of blood through the person's body. The ribbing applied to the upper surface of the envelope enables the user to move his or her feet over the surface of the ribbing again to stimulate blood circulation.

In another aspect, the invention provides apparatus for relieving the symptoms of deep vein thrombosis which comprises a fabric envelope having on one surface a plurality of projections and on an opposed surface means for releasably attaching the envelope to a floor surface, a container dimensioned to fit within the fabric envelope and comprising two side-by-side compartments which communicate with one another through one or more openings and a mouthpiece to enable the compartment to be inflated, and a pocket provided above one of the two compartments of the container dimensioned to receive a heating element.

The invention will now be described by way of example only with reference to the accompanying diagrammatic drawings in which.

Figure 1:
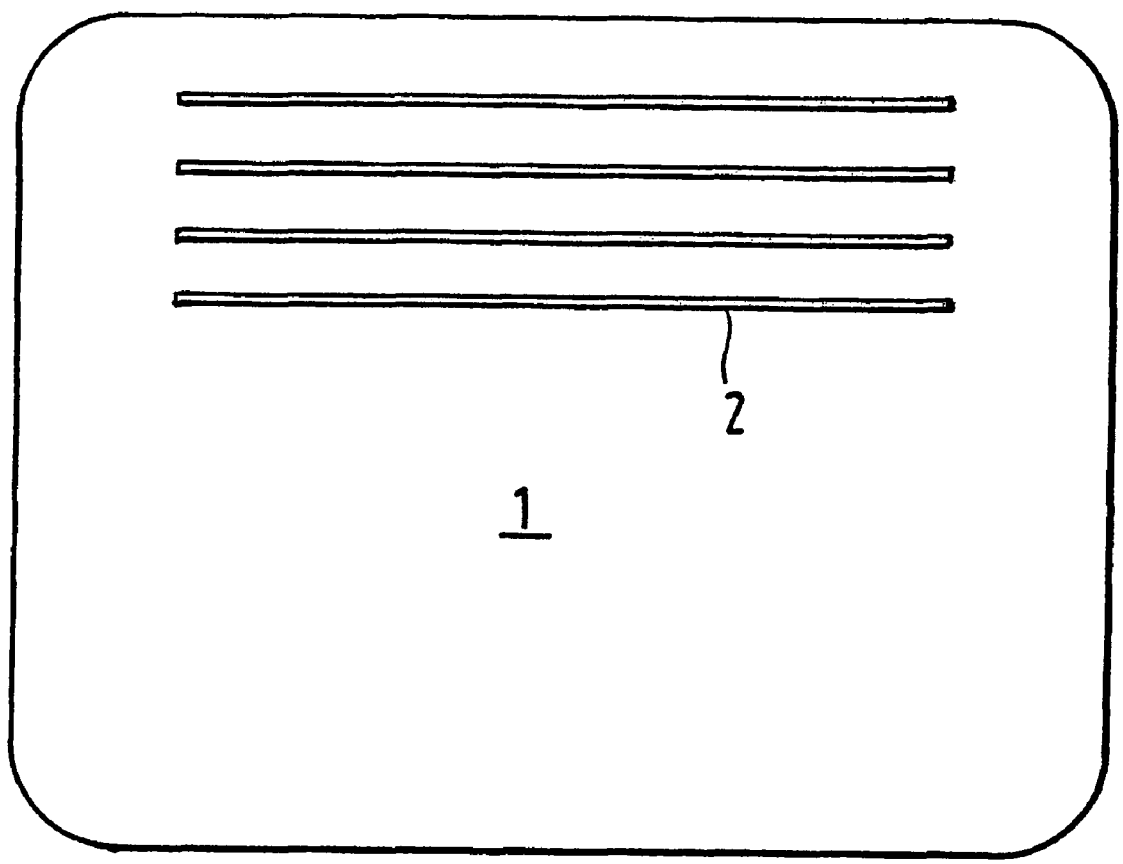
FIGS. 1 and 2 are respectively plan and side views of an envelope which forms part of apparatus in accordance with the invention.
Figure 2:
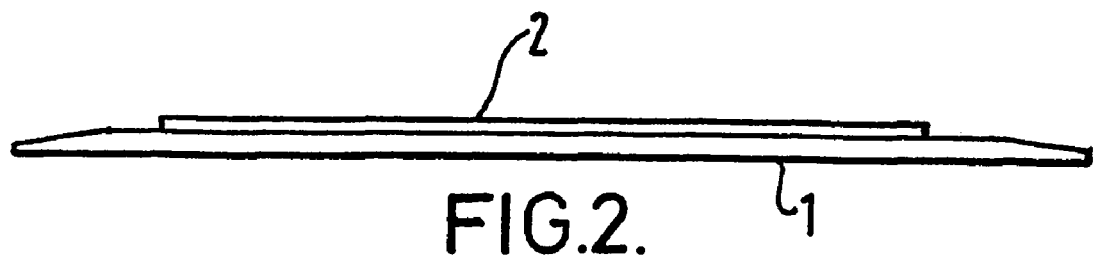

The apparatus for relieving symptoms of deep vein thrombosis illustrated in FIGS. 1 and 2 of the drawings comprises a fabric envelope 1 whose upper surface is formed with ribs 2. The ribs extend upwardly from pads secured to the upper surface of the envelope. The ribs may extend across the full width of the envelope. More or less ribs than shown may be provided. Typically, the height of each rib is or the order of 1.5 mm. A typical height range is between 1 mm and 3 mm. The ribs are typically produced from a plastics, synthetic rubber or a rubber substitute. The spacings between neighbouring ribs is sufficient to stimulate blood flow in stockinged or bare feet of a user when the feet are moved backwards and forwards over the ribs. Other patterns of ribs or projections may be used. For example, the pattern may take the form of a matrix.

The surface of the envelope remote from the ribs 2 carries strips of a hook and loop-type fastener sold under the trademark Velcro® (not shown) to enable the envelope to be attached to a carpeted floor surface.

Figure 3:
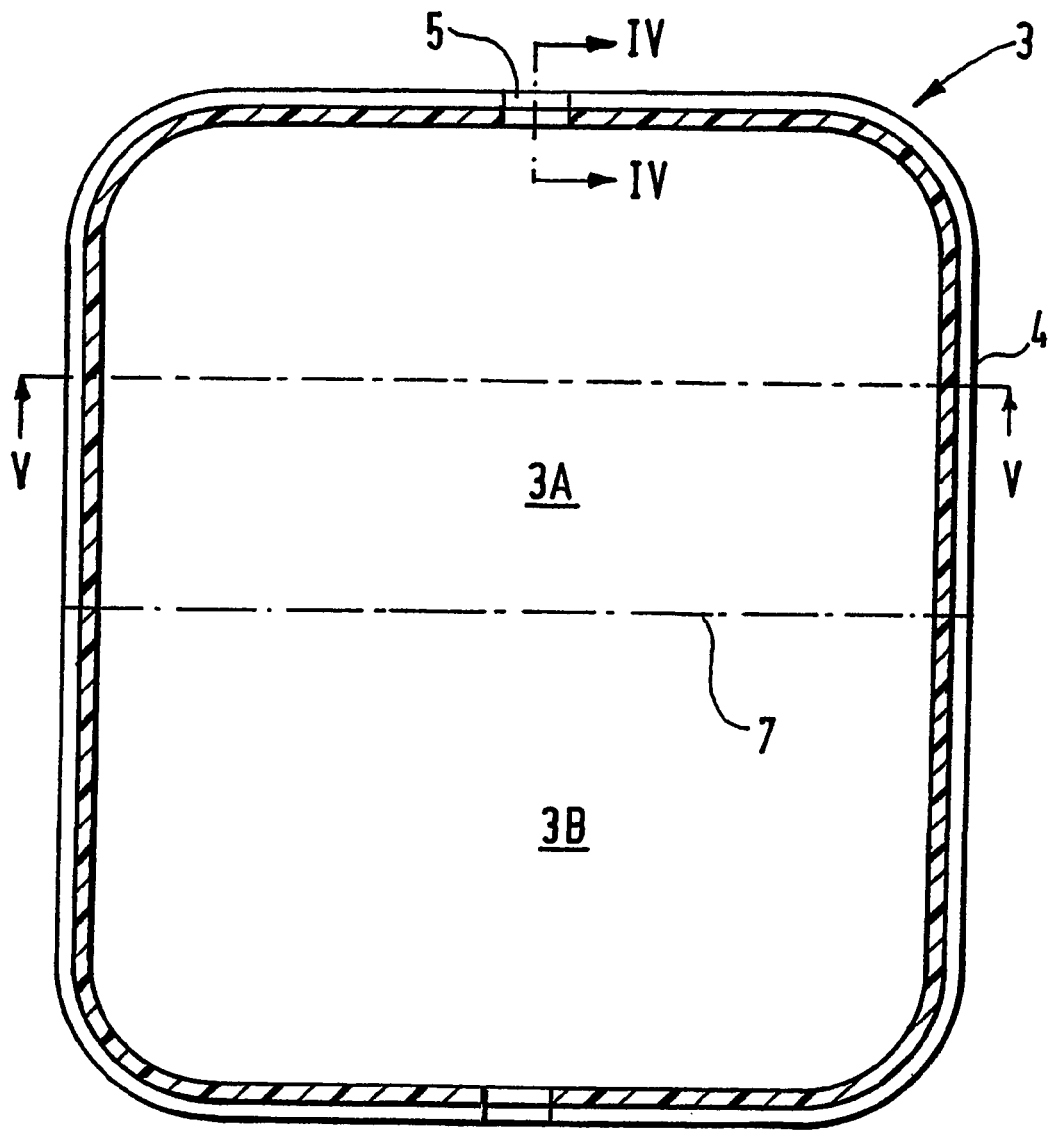
FIG. 3 is a section taken through a container forming part of apparatus in accordance with the invention.
Figure 4:
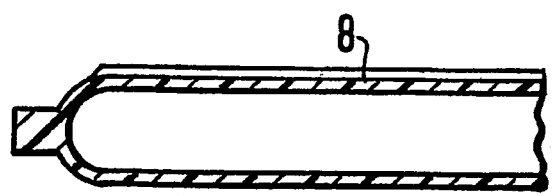
FIG. 4 is a partial section taken along line IV—IV of FIG. 3.
Figure 5:
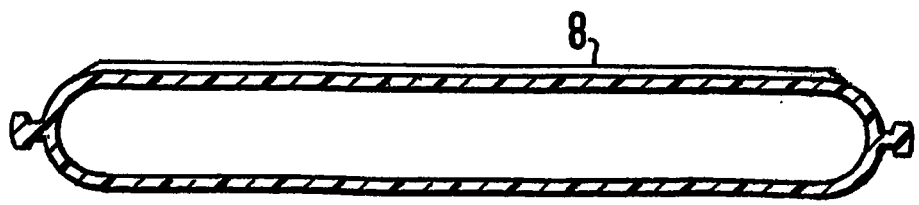
FIG. 5 is a section taken along lines V—V of FIG. 3.

The container 3 shown in FIGS. 3 to 5 is typically produced from plastics, a natural rubber or a rubber-like substitute material and comprises side ribs 4 and a closure 5 which either selectively or permanently seals the container interior. Typically, the thickness of the material is 1.25 mm. A typical range of thicknesses is from 1 mm to 2.5 mm. The container is divided into two side-by-side compartments 3A, 3B by an internal seam 7 (shown in broken line) which extends over the full width of the container. An external pocket extends over one of the compartment 3A. The compartment is dimensioned to receive a portable heat pack as described above. Each of the compartments 3A, 3B is partially filled with a flowable material, e.g. air, water or granular material.

Figure 6:
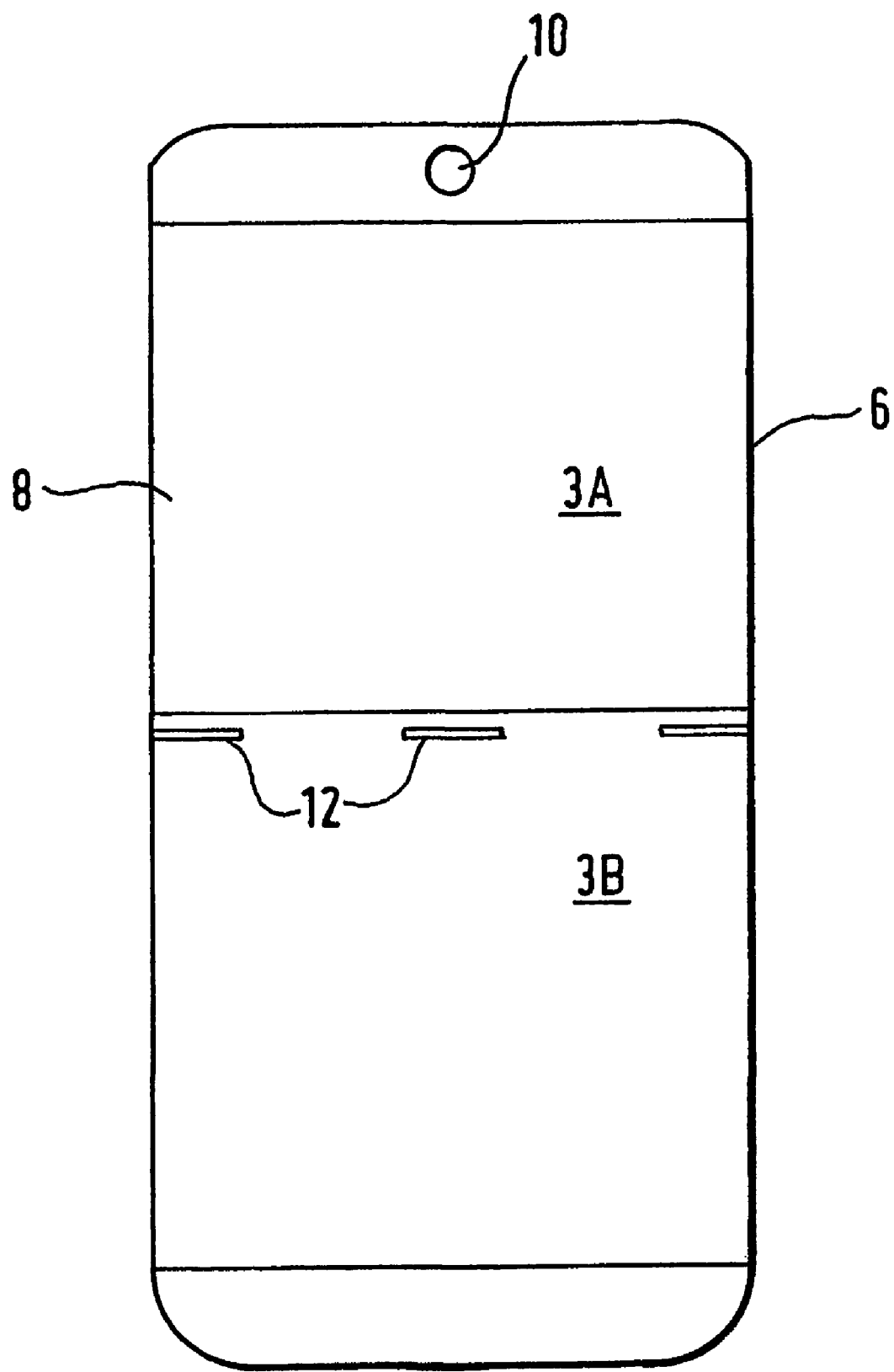
FIG. 6 is a plan view of alternative apparatus in accordance with the invention.

The alternative apparatus shown in FIG. 6 comprises a generally rectangular air filled container 6 divided along lateral seams 12 to define two compartments 3A, 3B. The seams extend over only a part of the lateral extent of the container, neighbouring seams defining discrete passageways for the flow of air from one compartment to the other. The seams may be created by a heat welding process. Pocket 8 is positioned above compartment 3A. This is defined between the upper surface of the container and a sheet of plastics or other material secured to the upper surface of the container. The dimensions of the pocket are sufficient to receive a portable heat pack.

A mouthpiece 10 is provided to enable the container to be partially inflated simply by the user blowing air by mouth in the compartments. In use, the container is positioned in the fabric envelope as described previously. One advantage of this embodiment is that depression of one compartment causes air to flow through the openings defined between the seams 12 to the other compartment thereby automatically lifting the respective foot of the user.

It will be appreciated that modifications can readily be made to the apparatus described without departing from the true scope of the invention as set out in the appended claims.

What is claimed is:

1. Apparatus for relieving the symptoms of deep vein thrombosis which comprises a container including first and second compartments each at least partially filled with a flowable material and each produced at least partially from a resilient material, an envelope having an underside and housing the compartments, and a pocket for receiving a heating element which overlies only one compartment of the container, an external surface of the envelope being formed with projections.

2. Apparatus as claimed in claim 1 wherein the compartments are separated by a seam which is partially discontinuous to define communicating passageways between the compartment interiors.

3. Apparatus as claimed in claim 1 wherein the container is produced from a rubber or resilient plastics material and is permanently sealed or fitted with a removable plug.

4. Apparatus as claimed in claim 1 wherein the flowable material is a fluid, a gas or a solid granular material.

5. Apparatus as claimed in claim 1 wherein the envelope is produced from a woven fabric.

6. Apparatus as claimed in claim 1 wherein the projections are produced from plastics, or natural or synthetic rubber.

7. Apparatus as claimed in claim 1 further comprising a heating element, wherein the heating element comprises a portable heat pack which comprises a sealed flexible plastic bag containing a chemically reactive substance and a metallic disc which when subjected to finger pressure or flexing produces a chemical reaction within the reactive substance to generate heat.

8. Apparatus as claimed in claim 1 wherein means are provided to attach the underside of the envelope to a floor surface.

9. Apparatus for relieving the symptoms of deep vein thrombosis which comprises a fabric envelope having on one surface a plurality of projections and on an opposed surface means for releasably attaching the envelope to a floor surface, a container dimensioned to fit within the fabric envelope and comprising two side-by-side compartments which communicate with one another through one or more openings and a mouthpiece to enable the compartment to be inflated, and a pocket provided above one of the two compartments of the container dimensioned to receive a heating element.

* * * * *